United States Patent
McMaster et al.

(10) Patent No.: US 10,126,222 B2
(45) Date of Patent: Nov. 13, 2018

(54) RHEOMETER SYSTEM WITH DECOUPLED CROSS-HEAD

(71) Applicant: Alpha Technologies Services LLC, Akron, OH (US)

(72) Inventors: Matthew S. McMaster, Wadsworth, OH (US); Keith Buzek, Akron, OH (US); William J. Roblin, III, North Royalton, OH (US)

(73) Assignee: ALPHA TECHNOLOGIES SEREVICES LLC, Akron, OH (US)

( * ) Notice: Subject to any disclaimer, the term of this patent is extended or adjusted under 35 U.S.C. 154(b) by 104 days.

(21) Appl. No.: 15/519,215

(22) PCT Filed: Oct. 8, 2015

(86) PCT No.: PCT/US2015/054675
§ 371 (c)(1),
(2) Date: Apr. 14, 2017

(87) PCT Pub. No.: WO2016/060928
PCT Pub. Date: Apr. 21, 2016

(65) Prior Publication Data
US 2017/0241884 A1    Aug. 24, 2017

Related U.S. Application Data

(60) Provisional application No. 62/063,624, filed on Oct. 14, 2014.

(51) Int. Cl.
*G01N 11/14* (2006.01)
*G01N 11/16* (2006.01)
*G01N 33/44* (2006.01)

(52) U.S. Cl.
CPC ......... *G01N 11/162* (2013.01); *G01N 33/442* (2013.01)

(58) Field of Classification Search
CPC ...... G01N 11/14; G01N 11/16; G01N 11/142; G01N 11/162; G01N 11/10
See application file for complete search history.

(56) References Cited

U.S. PATENT DOCUMENTS 3,279,240 A * 10/1966 Kowalski ............... G01N 11/04
374/51
3,479,858 A * 11/1969 Miyake ............... G01N 11/165
374/48

(Continued)

FOREIGN PATENT DOCUMENTS

JP        09329539 A  * 12/1997
WO    WO 2007/149435 A2    12/2007

OTHER PUBLICATIONS

Extended European Search Report for European Application No. 15850581.8, dated Jan. 31, 2018.

(Continued)

*Primary Examiner* — David A Rogers
(74) *Attorney, Agent, or Firm* — Shumaker, Loop & Kendrick, LLP; James D. Miller

(57) ABSTRACT

The present application relates generally rheometers. In one aspect, misalignment of the air cylinder with respect to the cross-head is accommodated using a flexible coupling between the air cylinder and the cross-head so as to prevent binding and stuttering of the machine due to misalignment.

6 Claims, 3 Drawing Sheets

(56) References Cited

U.S. PATENT DOCUMENTS

| | | | | |
|---|---|---|---|---|
| 3,488,992 | A * | 1/1970 | Mehrbrodt | G01N 11/165 374/48 |
| 3,531,996 | A * | 10/1970 | Harris | B29C 35/0288 374/48 |
| 3,681,980 | A * | 8/1972 | Decker | G01N 3/34 374/48 |
| 3,688,568 | A * | 9/1972 | Paul | G01N 11/165 374/47 |
| 3,818,751 | A * | 6/1974 | Karper | G01N 11/10 374/46 |
| 4,343,190 | A | 8/1982 | Danko et al. | |
| 4,552,025 | A * | 11/1985 | Barker | G01N 11/165 374/47 |
| 4,559,812 | A * | 12/1985 | Kitchen | G01N 11/14 374/47 |
| 5,103,679 | A | 4/1992 | Porter et al. | |
| 5,253,513 | A * | 10/1993 | Van Arsdale | G01N 11/16 73/54.02 |
| 5,349,847 | A * | 9/1994 | Lee | G01N 11/142 73/54.28 |
| 5,481,903 | A * | 1/1996 | King | G01N 11/165 73/54.16 |
| 5,526,693 | A * | 6/1996 | Wise | G01N 11/165 73/54.39 |
| 5,610,325 | A * | 3/1997 | Rajagopal | G01N 11/142 73/54.35 |
| 5,631,409 | A | 5/1997 | Rajagopal et al. | |
| 6,681,617 | B1 | 1/2004 | Putman et al. | |
| 9,513,202 | B2 * | 12/2016 | Mak | G01N 11/14 |
| 2008/0062212 | A1 * | 3/2008 | Na | B41F 31/005 347/6 |
| 2014/0260558 | A1 * | 9/2014 | McMaster | G01N 11/165 73/54.01 |
| 2015/0198512 | A1 * | 7/2015 | Montgomery | G01N 11/14 73/843 |
| 2017/0212025 | A1 * | 7/2017 | Pileggi | G01N 33/383 |
| 2017/0241885 | A1 * | 8/2017 | Buzek | G01N 11/162 |

OTHER PUBLICATIONS

International Search Report and Written Opinion for International Application No. PCT/US2015/054675, dated Dec. 29, 2015.
International Preliminary Report on Patentability for International Application No. PCT/US2015/054675, dated Apr. 27, 2017.

* cited by examiner

RHEOMETER SYSTEM WITH DECOUPLED CROSS-HEAD

CROSS REFERENCE TO RELATED APPLICATIONS

This application is a 371 U.S. National Stage of International Application No. PCT/US2015/054675 filed on Oct. 8, 2015, which claims the benefit of U.S. provisional application no. 62/063624, filed on Oct. 14, 2014, both of which are incorporated by reference herein in their entirety.

BACKGROUND

1. Field

Aspects herein generally relate to rheometer systems for testing polymers, and more particularly to a decoupled cross-head incorporated into a rheometer system.

2. Discussion of Related Art

Polymers are often tested according to one of several ASTM methods, namely, ASTM D1646, D2084, D5289, and D6204. Instruments operating in accordance with ASTM D2084 and D5289 are known. For example, U.S. Pat. No. 3,681,980 illustrates the application of a fixed eccentric cam to facilitate oscillation of a rotor. This amplitude of oscillation is determined by the position of the pin on the eccentric. U.S. Pat. No. 4,794,788 also illustrates the use of an eccentric to facilitate an oscillatory motion. The amplitude of oscillation can be changed between tests by changing the position of the pin on the eccentric or by changing the eccentric to one with a different off-set.

ASTM D6204 describes the use of a variable frequency test, and also discloses the capability of performing a variable temperature test. ASTM D6601 describes the conditions for evaluating a specimen at more than one strain amplitude during a single test. This test may be used with the apparatus described in U.S. Pat. Nos. 4,794,788, 5,079,956 or 6,681,617.

Many of the apparatus described in these patents and used in the foregoing ASTM test methods are referred to as moving die rheometers. In typical moving die rheometers, two opposing co-axial dies compress a test specimen between them. One die is driven in an oscillatory manner, while the opposite die is free to rotate independently of the first die. A flex arm is connected to the one die, and this flex arm is driven back and forth to create the oscillatory movement of the one die. In these existing systems, a drive system may comprise an eccentric attached to the output of a motor. The eccentric is connected to a link arm which is further connected to a flex arm. The amplitude of movement of the one die is determined by the distance between the axis of rotation of the eccentric and the post of the eccentric.

In other rheometer systems, the drive shaft of the motor may be directly coupled to the one die without the use of any link arms. The desired oscillatory motion is produced by the motor.

Both types of rheometers may employ a moving cross-head driven by an air cylinder to urge the opposite die toward the one die to compress a test specimen between the two dies. In existing systems, the cylinder shaft is rigidly coupled to the cross-head. In such systems, the system frequently stutters or binds up, causing problems. Also, alignment of the two opposing coaxial dies is sometimes difficult to maintain.

SUMMARY OF INVENTION

One aspect of the invention relates to a rheometer system that includes one or more posts extending between two plates, a cross-head mounted on the posts, a drive apparatus which moves the cross-head upwardly and downwardly along the posts, an upper die disposed on the cross-head, a lower die disposed in spaced relation to the upper die, the upper and lower dies being configured to capture a test sample therebetween, and apparatus for coupling the drive apparatus to the cross-head to accommodate misalignment between the drive apparatus and the posts upon which the cross-head moves and to permit alignment of the upper die with the lower die. The coupling apparatus includes a connector having a shaft coupled to the drive apparatus, and a head enlarged with respect to the shaft, the head having a curved surface. The coupling apparatus also includes a flange disposed on the cross-head, in which the curved surface of the head bears against a surface on the flange, and a retainer having a lip overlying the head of the connector to limit upward movement of the head with respect to the surface of the flange, the lip of the retainer being spaced sufficiently from the connector to permit tilting movement of the connector with respect to the cross-head while still retaining the connector within the retainer as the cross-head moves upwardly and downwardly. In another embodiment of this aspect, the head of the connector resides in a recess on the flange. In another embodiment of this aspect, the head of the connector is spaced from inner surfaces of the recess on the flange. In yet another embodiment of this aspect, the drive apparatus is an air cylinder. In another embodiment of this aspect, the connector is a bolt.

Another aspect of this invention relates to a method in which the rheometer system has a cross-head that is mounted on posts and travels along the posts in a direction of elongation of the posts, a drive apparatus for moving the cross-head and a shaft that connects the drive apparatus to the cross-head. The method accommodates misalignment of the drive apparatus with respect to the posts and includes permitting the shaft connecting the cross-head to the driver apparatus to float with respect to the cross-head at an end of the shaft coupled to the cross-head.

BRIEF DESCRIPTION OF DRAWINGS

The accompanying drawings are not intended to be drawn to scale. In the drawings, each identical or nearly-identical component that is illustrated in various figures is represented by a like numeral. For purposes of clarity, not every component may be labeled in every drawing. Various embodiments of the invention will now be described by way of example with reference to the accompanying drawings, in which.

DETAILED DESCRIPTION OF THE INVENTION

This invention relates to an improved rheometer system for testing polymers. In one aspect an air cylinder is decoupled from the cross-head so that the cylinder can float relative to the cross-head.

Figure 1:
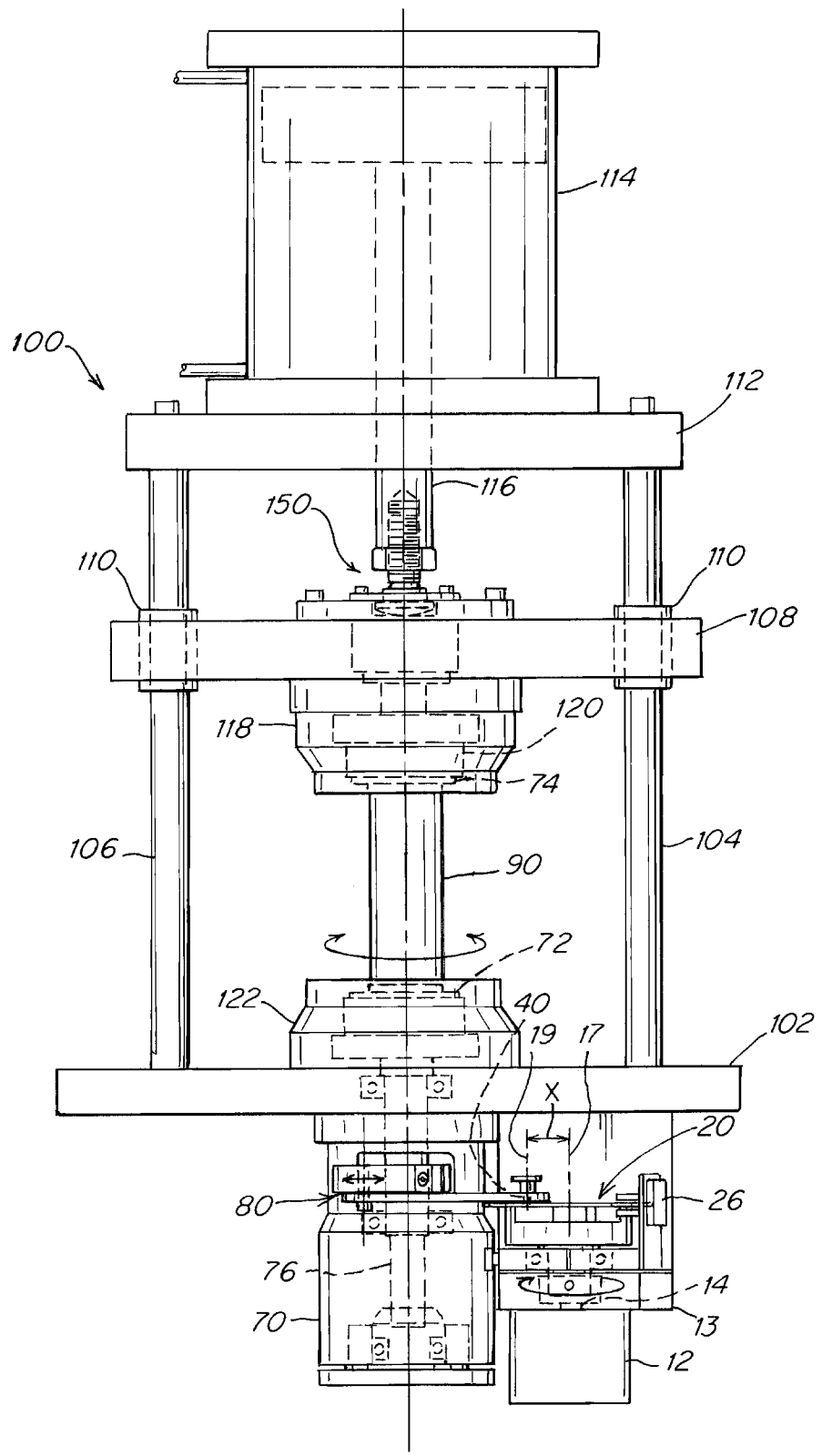
FIG. 1 is a front schematic view of one rheometer in accordance with one aspect of the invention.

With reference now to the drawings, and more particularly to FIG. 1 thereof, an embodiment of a moving die rheometer (MDR) will now be described. MDR 100 typically includes a main plate 102 and posts 104 and 106 mounted to and extending upwardly from main plate 102. A cross-head 108 rides upwardly and downwardly along one or more posts 104 and 106 on bearings 110. A cylinder mounting plate 112 sits on top of posts 104 and 106. Mounted on top of cylinder mounting plate 112 is an air or gas cylinder 114. Instead of an air cylinder, any other known drive apparatus could be used, such as an electric or gasoline motor, or a hydraulic system which is capable of moving cross-head 108 along posts 104 and 106. A shaft 116 extends downwardly from air cylinder 114 through cylinder mounting plate 112. Shaft 116 is mounted to cross-head 108 by a coupling system 150, which will be more fully described below, so as to allow air cylinder 114 to drive cross-head 108 upwardly and downwardly along posts 104 and 106. Suspended from cross-head 108 is an upper housing 118 which includes a torque transducer 120. Disposed on a lower end of upper housing 118 is an upper die 74.

Mounted onto main plate 102 is a lower housing 122, and disposed below lower housing 122 and mounted to main plate 102 is a central stack housing 70. Disposed on the upper end of lower housing 122 is lower sample die 72. Mounted on main plate 102 and disposed adjacent central stack housing 70 is a drive motor 12 which is coupled to an eccentric cam 20. Typically, eccentric cam 20 is a fixed eccentric cam, although cam 20 could also be a variable eccentric cam. Drive motor 12 rotates a drive shaft 14. Motor 12 is attached to motor mount 13. Drive shaft 14 is rigidly affixed to eccentric cam 20 so that rotation of drive shaft 14 is directly transferred to eccentric cam 20. Eccentric cam 20 has a central axis of rotation 17 passing through the center thereof, and through the center of drive shaft 14. A die shaft 76 passes through the center of central stack housing 70 and is rigidly affixed to sample die 72. Die shaft 76 in turn is coupled to eccentric cam 20, by link assembly 80. Link assembly 80 is coupled to post 40 on cam 20 at a distance X spaced from axis 17. The connection of link assembly 80 to post 40 causes the link assembly 80 to rotate about an axis 19 to produce the desired eccentric motion. Rotation of drive shaft 14 by motor 12 causes rotation of eccentric cam 20, which causes link assembly 80 to move in an oscillatory motion, which motion is then transferred by link assembly 80 through die shaft 76 to lower sample die 72. The amount of the oscillatory motion is referred to as the strain angle and is a function of distance X.

During testing of a polymer specimen 90, specimen 90 is positioned on lower sample die. When air cylinder 114 is activated, cylinder shaft 116 drives cross-head 108 downwardly to urge upper die 74 against the polymer specimen 90 and to capture and compress specimen 90 between lower die 72 and upper die 74. Oscillatory motion is then produced on lower die 72. During testing, heat may be applied to the specimen 90 in a conventional manner. Torque transducer 120 measures the reaction torque that is the result of the resistance of the polymer specimen 90 to the oscillatory motion. A test method that may be used with MDR 100, is described by ASTM D5289. When employing MDR 100, a measurement would first be made at one amplitude of oscillation, and after a change in the amplitude of oscillation, another measurement would be made, and so forth.

Figure 2:
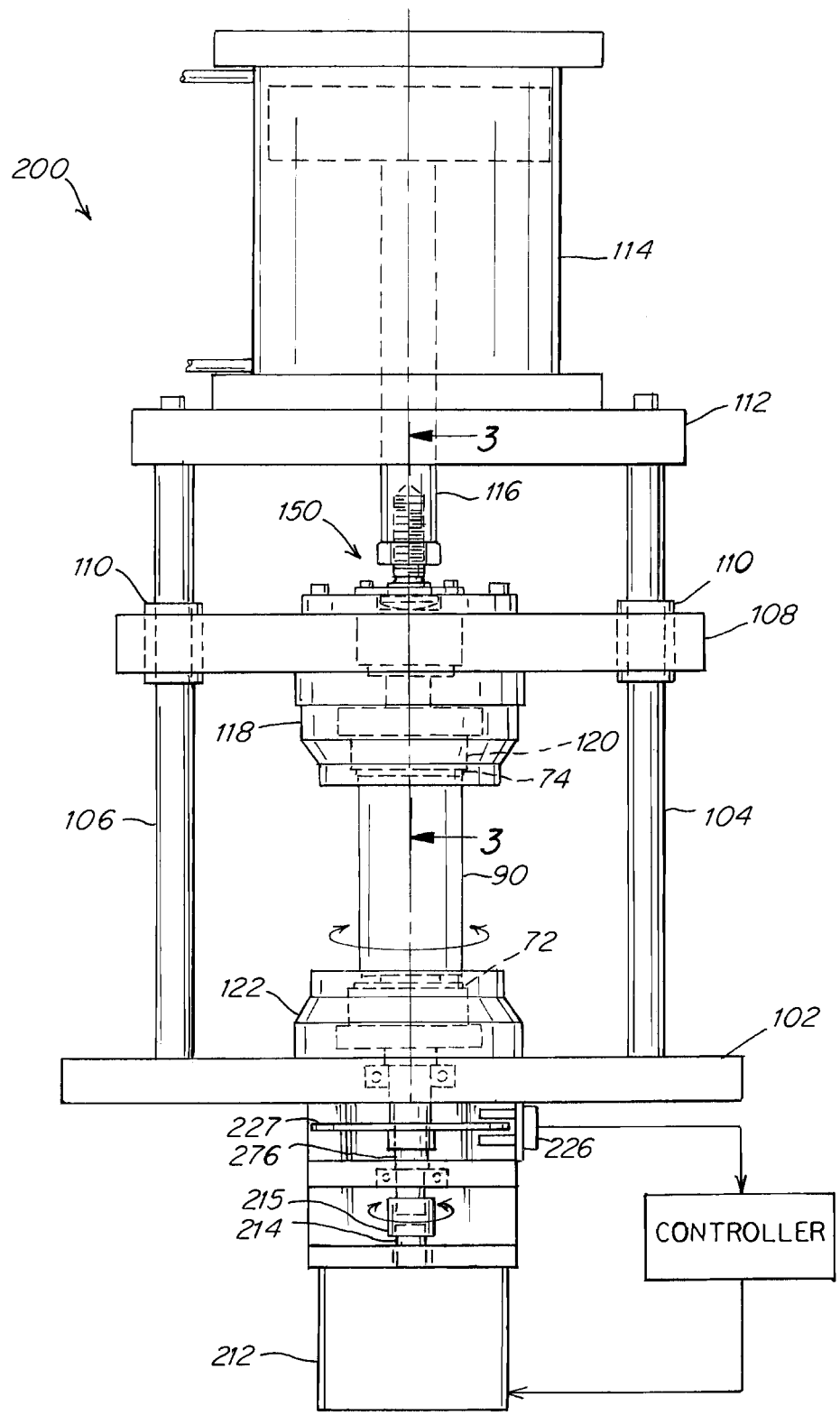
FIG. 2 is a front schematic view of another rheometer in accordance with another aspect of the invention.

Another embodiment of a rheometer with which the decoupled cross-head of this invention may be used will now be described with particular reference to FIG. 2. Rheometer 200 is commonly known as a dynamic mechanical rheological tester or DMRT which is designed to test raw elastomers or mixed rubber. Rheometer 200 is similar in many aspects to MDR 100, and where possible, like numbers will be used for like parts for simplicity and ease of understanding. Like MDR 100, rheometer 200 typically includes a main plate 102, and posts 104 and 106 mounted to and extending upwardly from main plate 102. A cross-head 108 rides upwardly and downwardly along posts 104 and 106 on bearings 110. A cylinder mounting plate 112 may sit on top of post 104 and 106. Mounted on top of the cylinder mounting plate is an air cylinder 114. A cylinder shaft 116 extends downwardly from air cylinder 114 through cylinder mounting plate 112. Cylinder shaft 116 is mounted to cross-head 108 by a coupling system 150, which will be more fully described below with respect to FIG. 3. Cylinder shaft 116 allows air cylinder 114 to drive cross-head 108 upwardly and downwardly along posts 104 and 106. Suspended from cross-head 108 is an upper housing 118 which includes a torque transducer 120. Disposed on a lower end of upper housing 118 is an upper die 74. Mounted onto main plate 102 is a lower housing 122, and disposed in the upper part of lower housing 122 is a lower sample die 72 that faces upper die 74.

Disposed below main plate 102 is a direct drive stepper motor 212, from which a drive shaft 214 extends. Shaft 214 is coupled to a lower die shaft 276 by coupling 215. Die shaft 276 passes through main plate 102 and is rigidly affixed to lower sample die 72. Die shaft 276 is rotated by stepper motor 212. An encoder 226 and encoder disk 227 determine the speed of rotation of die shaft 276, as well as the position of die shaft 276. Encoder 226 and encoder disk 227 may be any known encoder. Die shaft 276 in turn causes movement or oscillation of lower sample die 72.

Testing of a specimen 90 is similar to the testing of polymer specimen 90 that is described with respect to FIG. 1. Specimen 90 is positioned on lower sample die 72. Air cylinder 114 is then activated to cause cylinder shaft 116 to drive cross-head 108 and upper housing 118 downwardly to urge upper die 74 against specimen 90 to capture and compress specimen 90 between lower sample die 72 and upper die 74. The desired oscillatory motion is then produced on lower die 72 by stepper motor 212. During testing, heat may be applied to the specimen 90 in a conventional manner. Torque transducer 120 measures the reaction torque that is a result of the resistance of the specimen 90 to the oscillatory motion. Test methods that may be used in conjunction with rheometer 200 include ASTM D5289, ASTM D6204, and ASTM D7605.

Figure 3:
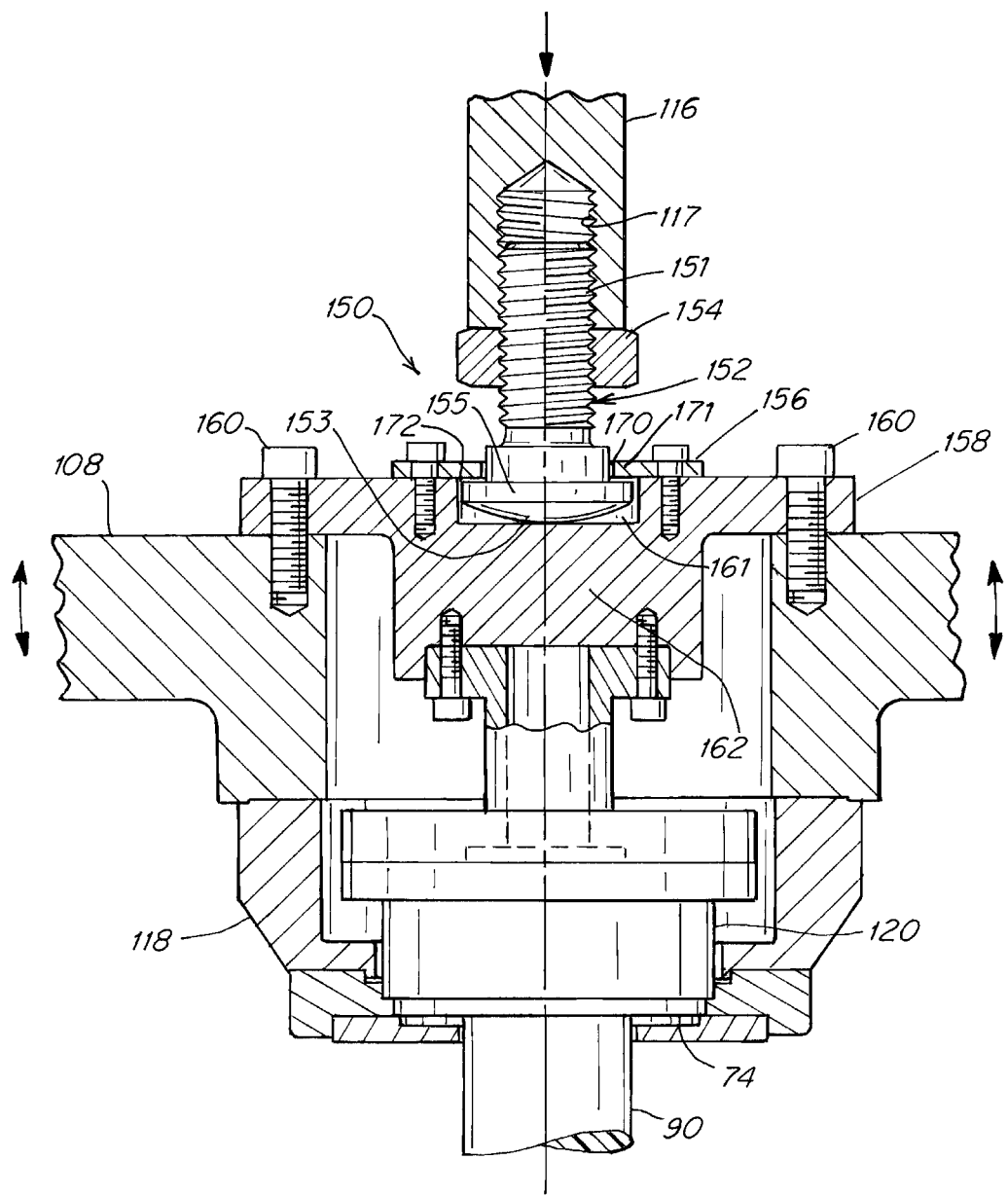
FIG. 3 is a partial, cross-sectional view of the decoupled cross-head taken along the line 3-3 of FIG. 2.

Both MDR 100, and rheometer 200 may include the same coupling system 150, which will now be described in another aspect of the invention with particular reference to FIG. 3. The description of coupling system 150 in FIG. 3 applies to both MDR 100 and rheometer 200. This same coupling system 150 also could be used with other rheometer systems not described herein.

In existing rheometer systems, cylinder shaft 116 often is rigidly coupled to cross-head 108. Cylinder shaft 116 is effectively a part of cross-head 108. As a consequence, the assembler and user of such an existing rheometer system had to make sure that air cylinder 114 and posts 104 and 106 were properly aligned. If air cylinder 114 were not properly aligned with respect to cylinder mounting plate 112 and/or posts 104 and 106, the system would stutter or even bind up as cross-head 108 moved upwardly and downwardly on posts 104 and 106. Also, even if the cylinder 114 and posts 104 and 106 were properly aligned, upper die 74 could be randomly positioned with respect to lower sample die 72. This result made it nearly impossible to align lower sample die 72 and upper die 74 and to still prevent the system from stuttering and/or binding up.

These problems are overcome by the use of coupling system 150. Coupling system 150 may include a connector such as a connector 152, a jam nut 154, a retainer 156, a flange 158 and bolts 160. Connector 152 may be a bolt and includes a shaft 151 and an enlarged head 155 which has an outer dimension or diameter larger than the diameter of shaft 151. Shaft 151 is coupled to cylinder shaft 116, such as by welding, threads, or the like. In one embodiment, shaft 151 is threaded into an opening 117 in the bottom of cylinder shaft 116. When installed, jam nut 154 may be tightly screwed up against the bottom edge of cylinder shaft 116 to prevent any loosening of shaft 151 of connector 152 within opening 117 due to vibrations and the like. Head 155 of connector 152 has a lower curved surface 153 which may be hemispherical in shape. A flange 158 is mounted onto cross-head 108 such as by means of bolts 160. Alternatively, flange 158 may be formed as an integral part of cross-head 108. Upper housing 118 is mounted into cross-head 108. Flange 158 includes a central portion 162 to which torque transducer 120 and upper die 74 are coupled. Head 155 may reside in a recess 161 in the upper surface of portion 162. Recess 161 extends around the entire circumference of head 155 and may be circular in shape. Lower curved surface 153 of head 155 bears on a surface of recess 161 in portion 162 when cross-head 108 is forced downwardly by cylinder shaft 116. In other embodiments, head 155 could rest on an upper surface of portion 162. Surrounding head 155 is a retainer 156 which includes a lip 171 which overlies head 155 and limits upward vertical movement of head 155. Lip 171 prevents head 155 from lifting out of recess 161 when cross-head 108 is raised upwardly by cylinder shaft 116. Retainer 156 may be affixed to flange 158 and includes a central opening which accommodates connector 152. While lip 171 of retainer 156 overlies portions of head 155, there is a gap 170 between head 155 and lip 171 of retainer 156, and another gap 172 between head 155 and interior surfaces of recess 161 of flange 158. Gaps 170 and 172 extend around the entire circumference of head 155. These gaps 170 and 172 allow tilting or pivoting movement of connector 152 with respect to retainer 156 and flange 158. This movement thus allows cylinder shaft 116 and thus cylinder 114 to float with respect to cross-head 108 so that any misalignment between air cylinder shaft 116 and cross-head 108 may be accommodated without binding and/or stuttering of the machine. Therefore, upper die 74 can be properly aligned with lower sample die 72 without having a perfect alignment of air cylinder 14 with respect to cross-head 108 and posts 104 and 106. If there is any misalignment between air cylinder 114 and cross-head 108, it will be accommodated by the gaps 170 and 172 between flange 158 and retainer 156 with respect to connector 152 which permit connector 152 to tilt or move with respect to cross-head 108.

While connector 152 was described as having a hemispherical surface 153, surface 153 may not necessarily be precisely hemispherical. Surface 153 could have other curved shapes. Surface 153 may be semi-elliptical or any other suitable curved shape, so long as tilting movement of connector 152 with respect to cross-head 108 is permitted while maintaining a tight connection between connector 152 and flange 158 and retainer 156. The gaps 170 and 172 may be of any suitable size that permits accommodation of misalignment of cylinder shaft 116 and cross-head 108, and which takes into account the nature of the curvature on surface 153. A typical gap 170 and 172 would be approximately 1 mm or 0.040 inch. However, other smaller or larger gaps 170 and 172 may be provided so long as they allow the rheometer to function without stuttering or binding, and they allow alignment of upper die 74 with lower sample die 72.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A rheometer system comprising:
   one or more posts extending between two plates;
   a cross-head mounted on the posts, the cross-head being movable along the posts;
   a drive apparatus which moves the cross-head upwardly and downwardly along the posts;
   an upper die disposed on the cross-head;
   a lower die disposed in spaced relation to the upper die, the upper and lower dies being configured to capture a test sample therebetween; and;
   apparatus for coupling the drive apparatus to the cross-head to accommodate misalignment between the drive apparatus and the posts upon which the cross-head moves and to permit alignment of the upper die with the lower die, the coupling apparatus comprising:
   a connector having a shaft coupled to the drive apparatus, and a head enlarged with respect to the shaft, the head having a curved surface;
   a flange disposed on the cross-head, the curved surface of the head bearing against a surface on the flange; and
   a retainer having a lip overlying the head of the connector to limit upward movement of the head with respect to the surface of the flange, the lip of the retainer being spaced sufficiently from the connector to permit tilting movement of the connector with respect to the cross-head while still retaining the connector within the retainer as the cross-head moves upwardly and downwardly.

2. The rheometer system of claim 1 wherein the head of the connector resides in a recess on the flange.

3. The rheometer system of claim 2 wherein the head of the connector is spaced from inner surfaces of the recess on the flange.

4. The rheometer system of claim 1 wherein the drive apparatus is an air cylinder.

5. The rheometer system of claim 1 wherein the connector is a bolt.

6. In a rheometer system having a cross-head that is mounted on posts and that travels along the posts in a direction of elongation of the posts, a drive apparatus for moving the cross-head, and a shaft that connects the drive apparatus to the cross-head, a method of accomodating misalignment of the drive apparatus with respect to the posts comprising permitting the shaft connecting the cross-head to the drive apparatus to float with respect to the cross-head at an end of the shaft coupled to the cross-head.

* * * * *